(12) United States Patent
Harper et al.

(10) Patent No.: US 7,198,663 B2
(45) Date of Patent: Apr. 3, 2007

(54) WOOD PRESERVATIVE COMPOSITION

(75) Inventors: Thomas L. Harper, Middletown, NY (US); Boris Reznikov, Fair Lawn, NJ (US); Allan Rosenberg, South Orange, NJ (US)

(73) Assignee: Sommerville Acquisitions Co., Inc., Flemington, NJ (US)

( * ) Notice: Subject to any disclaimer, the term of this patent is extended or adjusted under 35 U.S.C. 154(b) by 36 days.

(21) Appl. No.: 11/111,432

(22) Filed: Apr. 21, 2005

(65) Prior Publication Data

US 2006/0011094 A1 Jan. 19, 2006

Related U.S. Application Data

(60) Provisional application No. 60/587,750, filed on Jul. 14, 2004.

(51) Int. Cl.
  *C09D 5/14* (2006.01)
  *B05D 1/00* (2006.01)
  *B05D 1/02* (2006.01)
  *A01N 59/06* (2006.01)
  *A01N 59/16* (2006.01)

(52) U.S. Cl. ............... 106/18.36; 106/15.05; 427/408; 427/419.2; 427/429; 427/430.1; 427/439; 427/440; 252/602; 252/607

(58) Field of Classification Search ...... None
See application file for complete search history.

(56) References Cited

U.S. PATENT DOCUMENTS

| | | | |
|---|---|---|---|
| 3,725,544 A | 4/1973 | Raff et al. | |
| 3,889,020 A | 6/1975 | Amundsen et al. | |
| 4,218,249 A | 8/1980 | Hill | |
| 4,303,726 A | 12/1981 | Turner | |
| 4,737,491 A | 4/1988 | Leppavuori et al. | |
| 4,783,221 A | 11/1988 | Grove | |
| 5,612,094 A * | 3/1997 | Schubert et al. | 427/397 |
| 5,733,666 A | 3/1998 | Sinko | |
| 5,879,437 A * | 3/1999 | Hartman | 106/14.44 |
| 6,441,016 B2 | 8/2002 | Gottschalk et al. | |
| 6,503,936 B1 | 1/2003 | Schelberger et al. | |
| 6,541,038 B1 | 4/2003 | Tanaka et al. | |
| 6,579,354 B1 | 6/2003 | West | |
| 2001/0027219 A1* | 10/2001 | Holcomb | 516/98 |
| 2002/0007926 A1 | 1/2002 | Jewell et al. | |
| 2002/0071806 A1 | 6/2002 | Sabacky et al. | |
| 2003/0041983 A1 | 3/2003 | Jewell et al. | |
| 2004/0055719 A1 | 3/2004 | Jewell et al. | |
| 2004/0166246 A1* | 8/2004 | Holcomb | 427/440 |
| 2004/0258768 A1 | 12/2004 | Hodge et al. | |

* cited by examiner

*Primary Examiner*—Joseph D. Anthony
(74) *Attorney, Agent, or Firm*—Caesar, Rivise, Bernstein, Cohen & Pokotilow, Ltd.

(57) ABSTRACT

An aqueous wood preservation composition containing inorganic polymers of one or more of the following metals is disclosed; aluminum (approximately 3.8%–7.0% as $Al_2O_3$), zirconium (approximately 5.25%–9.1% as $ZrO_2$), copper (approximately 0.7%–8.8% as CuO) and a fixing agent such as acetic acid or sodium acetate. The pH is adjusted to be between 2.0–4.0 using an inorganic base such as copper carbonate. The invention includes wood and cellulose fibers treated by the composition of the present invention as well as methods of preserving wood and cellulose fibers using the compositions.

24 Claims, No Drawings

WOOD PRESERVATIVE COMPOSITION

CROSS-REFERENCE TO RELATED APPLICATIONS

This utility application claims the benefit under 35 U.S.C. §119(e) of Provisional Application Ser. No. 60/587,750 filed on Jul. 14, 2004 entitled WOOD PRESERVATIVE COMPOSITION, whose entire disclosure is incorporated by reference herein.

BACKGROUND OF THE INVENTION

1. Field of Invention

This invention relates generally to wood preservative compositions containing metal compounds that are environmentally safe and methods of treating wood and other cellulose fibers using those compositions.

2. Description of Related Art

The following prior art references are incorporated in their entirety herein. Wood preservative compositions of aqueous solutions containing metal compounds have been used for many applications. The wood preservation solution is applied by various methods including, injection in pressure vessels, immersion in open vessels, and by brushing or spray painting onto the wood surface or other cellulose fiber.

Compounds used as the active ingredient in wood preservation solutions include copper compounds, such as, but not limited to copper acetate; chrome compounds, such as, but not limited to potassium chromate; and arsenic compounds, such as but not limited to, arsenious acid. (for example see U.S. Pat. No. 5,207,583). CCA (Copper, chromium, arsenic) wood preservatives have produced good protection against wood decay, but are not environmentally safe.

The copper and arsenic provide fungicidal activity and the chromium acts to fix the copper to the wood. Aluminum compounds, such as aluminum halohydrates provide improved water repellency of cellulose when used as a component of CCA formulations (U.S. Pat. No. 4,212,249).

Zirconium complexes have also been shown to provide water repellency and enhance the antimicrobial action of copper. According to U.S. Pat. No. 4,737,491, the zirconium complex may be added as a separate salt or incorporated into a metal amine polymer and complex. The penetration of these complexes is limited by polymer molecular weight and configuration. Hydrophobic components in the formulation will decrease the effectiveness of the solution.

Zirconium has also been described as an inert fixing agent for borates in wood preservation compositions (U.S. Pat. No. 5,612,094). This approach has proven ineffective. In some cases a fixing agent such as acetic acid is added to the wood preservative formulation. When these formulations are applied to wood a series of reactions take place between the components of the preservative solution (ie fixing agent, metal) and the wood fibers. These reactions fix the preservative to the wood resulting in improved resistance to leaching. Unfortunately this method also reduces penetration and diminishes the activity of the preservative.

U.S. Pat. No. 3,725,544 (Raff et al.) discloses that aluminum based wood preservatives may have other metals.

U.S. Pat. No. 3,889,020 (Amundsen et al.) discloses treating wooden objects with a blend of pentachlorophenol and a petroleum hydrocarbon in claimed amounts. The compositions as disclosed in column 3, may also contain zirconium and copper, but not aluminum.

U.S. Pat. No. 4,212,249 discloses aluminum compounds, such as aluminum halohydrates that apparently provide improved water repellency of cellulose when used as a component of CCA formulations. Zirconium complexes have also been shown to provide water repellency and enhance the antimicrobial action of copper.

U.S. Pat. No. 4,218,249 (Hill) discloses copper and aluminum mixed with chromium hexavalent and even copper-arsenic mixtures.

U.S. Pat. No. 4,303,726 (Turner) discloses an aluminum based wood preservative that may have additional divalent metals such as zinc and at least one carboxylic acid radical.

U.S. Pat. No. 4,737,491 (Leppavuori) discloses that a zirconium complex may be added as a separate salt or incorporated into a metal amine polymer and complex. The penetration of these complexes is limited by polymer molecular weight and configuration. Hydrophobic components in the formulation will decrease the effectiveness of the solution.

U.S. Pat. No. 4,783,221 (Grove) discloses an organic compound based wood preservative composition comprising at least one metal salt of an organic carboxylic acid containing at least about 6 carbon atoms, wherein the metal may be zinc, mercury, antimony and lead, and at least one isothiazolone compound.

U.S. Pat. No. 5,207,583 discloses wood preservative compositions of aqueous solutions containing metal compounds. The wood preservation solution is applied by various methods including, injection in pressure vessels, immersion in open vessels, and by brushing or spray painting on a wood surface. Compounds used as the active ingredient in wood preservation solutions include; copper compounds, such as copper acetate; chrome compounds, such as potassium chromate; and arsenic compounds, such as arsenious acid. (for example see CCA (Copper, chromium, arsenic) wood preservatives have produced good protection against wood decay, but are not environmentally safe. The copper and arsenic provide fungicidal activity and the chromium acts to fix the copper to the wood.

U.S. Pat. No. 5,612,094 (Schubert et al.) discloses that zirconium has also been described as an inert fixing agent for borates in wood preservation compositions. In some cases a fixing agent such as acetic acid is added to the wood preservative formulation. When these formulations are applied to wood, a series of reactions take place between the components of the preservative solution (i.e., fixing agent, metal) and the wood fibers. These reactions fix the preservative to the wood resulting in improved resistance to leaching. Unfortunately, this method also reduces penetration and diminishes the activity of the preservative.

U.S. Pat. No. 5,733,666 (Sinko) discloses a composition to reduce the staining of coatings comprising a zirconyl compound in a liquid, and a lanthanide compound to provide UV protection. Additional metals such as chromium and copper and aluminum are disclosed.

U.S. Pat. No. 6,441,016 (Gottschalk et al.) discloses a wood preservative of copper and an alkanolamine and cyproconazole and an emulsifier.

U.S. Pat. No. 6,503,936 (Schelberger et al.) discloses a wood preservative of metals such as aluminum and copper, but zirconium is not detailed. The claims discuss a fungicidal composition of the formula I carbamate and a copper-containing fungicidal active compound, where they are present in synergistically effective amounts.

U.S. Pat. No. 6,541,038 (Tanaka et al.) discloses a metal ion based wood preservative containing zirconium, copper and aluminum, but also as fire retardants. The formulations also contain lignin and/or lignin derivatives to fix the metal in the wood.

U.S. Pat. No. 6,579,354 (West) discloses copper and aluminum based wood preservatives without zinc base and without environmentally challenged hexavalent chromium. The composition includes a water soluble acidic copper pesticide combined with aluminum nitrate wherein the weight ratio of aluminum nitrate to copper is from a:10 to 10:1.

U.S. Pat. No. 6,623,552 (West) discloses aluminum based wood protectives, but without copper or zirconium to protect the wood from UV degradation and agents.

U.S. Published Application No. 2002/0007926 (Jewell et al.) discloses copper based biocidals for cellulose fibers, but does not disclose aluminum or zirconium.

U.S. Published Application No. 2002/0071806 (Sabacky et al.) discloses methods of making metal salt mixtures but not directed to wood preservatives.

U.S. Published Application No. 2003/0041983 (Jewell et al.) discloses copper based biocidal for celluose fibers such as wood pulp, but does not disclose aluminum or zirconium.

U.S. Published Application No. 2004/0055719 (Jewell et al.) discloses copper based biocidal for cellulose fibers such as wood pulp, but does not disclose aluminum or zirconium.

U.S. Published Application No. 2004/0258768 (Hodge et al.) discloses copper based wood preservatives that may have other metal ions but zirconium and aluminum are not disclosed.

BRIEF SUMMARY OF THE INVENTION

An aqueous wood preservation composition contains inorganic polymers of one or more of the following metals: aluminum (approximately 3.8%–7.0as $Al_2O_3$), zirconium (approximately 5.25%–9.1% as $ZrO_2$), copper (approximately 0.7%–8.8% as CuO) and a fixing agent such as acetic acid or sodium acetate. The metals may be supplied in various forms and are not intended to be limited to the ones specified herein.

The pH is adjusted to be between 2.0–4.0 using an inorganic base such as copper carbonate. It is believed the copper will be incorporated into the structure of the aluminum and zirconium polymers by bonding to oxygen attached to the other metals, although this proposed theory is not intended as a limitation on the invention. The pH dictates the molecular weight range of the polymer species.

The composition of the present invention maintains a molecular weight of approximately 1000–2000 for the aluminum/copper polymers and approximately 6000–8000 for the zirconium/copper polymers. The smaller aluminum based polymers provide deep penetration carrying the copper into the wood and/or cellulose fibers to maximize efficacy. The larger zirconium polymers do not penetrate as deeply providing efficacy and water repellency to the outer layers of the treated wood/fibers. The acetate based fixing agent serves to improve the resistance to leaching by bonding the aluminum and zirconium polymer backbone to cellulose fibers in the wood. This novel blend of polymer species results in an improvement over current technology.

DETAILED DESCRIPTION OF THE INVENTION

The present invention provides an environmentally sound wood preservative composition with superior resistance to leaching without compromising penetration and effectiveness.

An aqueous wood preservation composition containing inorganic polymers of one or more of the following metals: aluminum (approximately 3.8%–7.0% as $Al_2O_3$), zirconium (approximately 5.25%–9.1% as $ZrO_2$), copper (approximately 0.7%–8.8% as CuO) and a fixing agent such as acetic acid or sodium acetate.

The pH is adjusted to be between 2.0–4.0 using an inorganic base such as copper carbonate. It is believed the copper will be incorporated into the structure of the aluminum or zirconium polymers by bonding to oxygen attached to the other metals. Proof or disproof of this theory has no impact on the practical value of this invention. The pH dictates the molecular weight range of the polymer species.

The composition of the present invention has a molecular weight of approximately 1000–2000 for the aluminum/copper polymers and approximately 6000–8000 for the zirconium/copper polymers. The smaller aluminum based polymers provide deep penetration carrying the copper into the wood to maximize efficacy. The larger zirconium polymers do not penetrate as deeply providing efficacy and water repellency to the outer layers of the treated wood. The acetate based fixing agent serves to improve the resistance to teaching by bonding the aluminum and zirconium polymer backbone to cellulose fibers in the wood. This novel blend of polymer species results in an improvement over current technology.

Method Summary

A wood preservation composition is prepared by preparing an aqueous solution of acetic acid and sodium acetate to provide approximately 2.0%–6.0% acetic acid and approximately 0.25% to 1.75% sodium acetate in the final composition. The solution should be mixed until fully dissolved. The solution will be clear with a slight yellow tint. A zirconium salt such as zirconium oxychioride that will provide a molecular weight of approximately 6000–8000 is selected. The salt is added to the acetate mixture such that the zirconium concentration in the final composition will be approximately 5.25%–9.1% as zirconium oxide. The solution is mixed until the zirconium salt is fully dissolved. The solution should be a clear yellow liquid. Next, HCl, preferably, 20 baume HCl is added such that the HCl concentration in the final composition is approximately 16%–20%. The solution will reach about 60–70° C. and must be cooled to about 25° C. before the next step. An aluminum salt such as polyaluminum chloride that will provide a molecular weight of approximately 1000–2000 is selected. The aluminum salt is added slowly to maintain a solution temperature of no greater than about 45° C., such that aluminum concentration in the final composition is approximately 3.8%–7.0% as aluminum oxide. The solution should be mixed until the temperature reduces to about 25° C. Copper carbonate is now added such that the copper concentration in the final composition will be approximately 0.7–8.8% as copper oxide. The pH of the final solution is to be between about 2.0–4.0. Continue to mix slowly until carbon dioxide liberation ceases. The solution should be a clear dark green. The final wood preservation solution is now ready for wood application by any of the methods known in the prior art, e.g., direct application, spraying, painting, injecting, etc.

EXAMPLE 1

In a 2000 ml glass reaction vessel, add 700 grams water and 15 grams of sodium acetate. Mix for 40 minutes or until the solution is clear. Add 50 grams acetic acid. Mix for 30 minutes. Add 420 grams zirconium oxychloride crystals. Mix for 30 minutes or until the solution is clear. The solution will have a molecular weight between 6,000 and 8,000 when tested with a Wyatt Dawn light scattering detector. Add 375 grams of 32% HCl and mix for two hours or until the temperature reduces to 25 degrees C. Add 460 grams poly-aluminum chloride at a rate to maintain a temperature at or below about 45 degrees C. Mix for two hours. The solution must be mixed until it cools to about 25 degrees C. Light scattering analysis of this solution indicates two distinct species. One at 6,000–8,000 and one at 1,000–2,000. Add 85 grams copper carbonate and mix well until all carbon dioxide evolution is complete.

The above composition was tested for efficacy and retention. The efficacy testing was performed in a 12 week treated/untreated, leached, unleached study verses *G. trabeum, P. placenta,* and *T. versicolor,* (standard fungi) Weight loss measurements were taken and found to show acceptable wood preservation relative to industry expectations. This same composition also showed excellent retention at all dilutions tested.

Experimental Results

The soil block test is a relatively rapid laboratory method for assessing the decay resistance of wood based materials under conditions that favor rapid fungal growth. Soil block tests of blocks treated with selected aluminum based compounds are now described.

Materials and Methods

Clear, defect-free southern pine (*Pinus taeda* L.) lumber was cut into 19 mm cubes. The cubes were oven-dried (40 degrees C.) then placed into beakers and weighted down. The beakers were filled with the test solution, then placed into a treatment vessel where they were subjected to a 30 minute vacuum followed by a 2 hour pressure period. The blocks were treated with WT 292 (example 1). WT 292 contains 3.2% aluminum and 6% zirconium. The concentrates were diluted 5:1, 10:1 or 20:1 with distilled water prior to treatment. After treatment, the blocks were removed from the pans, blotted to remove excess solution and weighed to determine net solution absorption. The blocks were then stored for 48 hours under non-drying conditions to facilitate any chemical/wood reactions before being oven-dried at 40 degrees C. and weighed. Each treatment was replicated on 36 blocks.

One half of the blocks in each treatment group were subjected to the leaching procedures described in A WPA Standard E-10, then soaked with water prior to being placed in plastic bags and sterilized by exposure to 2.5 mrad of ionizing radiation from a cobalt 60 source.

Decay chambers were prepared by half-filling 454 ml french squares with moisture forest loam and placing a western hemlock (for brown rot fungi) or red alder (for white rot fungi) feeder strip on the soil surface. The bottles were then loosely capped and autoclaved for 45 minutes at 121 degrees C. The bottles were allowed to cool overnight, then autoclaved again for 15 minutes at 121 degrees C. to kill any spore-forming bacteria.

After cooling, the bottles were inoculated with 2 to 3 mm diameter malt agar disks cut from the actively growing edges of cultures of the test fungus. The fungi evaluated in these procedures was *Postia placenta* (Fr.) *Larsen et Lombard* (Isolate Madison 698), *Gloeophyllum trabeum* (Pers.ex.Fr) Murr. (Isolate Madison 617), and *Trametes versicolor* L. ex Fr) *Pilat* (Isolate R-105). The first two species cause brown, while the latter causes white rot. The agar plugs were placed on the edges of the wood feeder strips, then the jars were loosely capped (to allow air exchange), and incubated until the feeder strip was thoroughly covered with fungal mycelium. The sterile test blocks were then placed, cross section down, on the surfaces of the feeder strips, the bottles were loosely capped and incubated at 28 degrees C. for 12 or 16 weeks, for the brown and white rot fungi, respectively.

At the end of the incubation period, the blocks were removed, scraped clean of adhering mycelium and weighed to determine wet weight. The blocks were then oven-dried (40 C) and weighed. The difference between initial and final oven-dry weight was used a measure of the effect of fungal exposure. At total of 234 blocks were tested using these procedures.

Results

Weight losses for the untreated controls ranged from 20 to 51% depending on the test fungus (Table 1). Low weight losses for the white rot fungus are not surprising since this fungus tends to be less aggressive on coniferous wood species, but even these weight losses were adequate for assessing treatment differences.

Weight losses of blocks treated with WT 292 were consistently below 5% regardless of the test fungus of treatment level, suggesting that the combination of zirconium and aluminum was an effective biocide. Leaching of blocks produced slight increases in weight loss, but even the leached levels were below 7% weight loss. These results indicate that this formulation exhibits some resistance to leaching.

The results clearly suggest that Formulation WT-292 has some potential as a wood preservative. It was effective against 3 common decay fungi and was resistant to leaching under laboratory conditions.

TABLE 1

Weight losses of treated and untreated southern pine blocks following 12 weeks of exposure to selected decay fungi in a soil block test:

| Chemical | Treatment Level | Leaching | Wood Weight Loss (%) *G. trabeum* | Wood Weight Loss (%) *P. placenta* | Wood Weight Loss (%) *T. versicolor* |
|---|---|---|---|---|---|
| Control | — | — | 28.38 (11.03) | 43.57 (11.88) | 20.55 (2.80) |
|  | — | yes | 48.14 (12.68) | 50.64 (10.09) | 13.35 (24.21) |
| WT-292 | 5:1 | — | 5.41 (0.22) | 5.32 (0.69) | 4.52 (1.34) |
|  |  | yes | 6.58 (0.32) | 7.37 (0.32) | 7.14 (0.67) |
|  | 10:1 | — | 3.57 (0.28) | 3.29 (0.21) | 3.61 (0.43) |
|  |  | yes | 6.66 (0.22) | 6.19 (0.26) | 5.88 (0.38) |
|  | 20:1 | — | 3.21 (0.44) | 1.88 (0.22) | 1.86 (0.82) |
|  |  | yes | 5.41 (1.02) | 2.41 (0.35) | 3.49 (0.84) |

Literature Cited

American Wood Preservers' Association (AWPA), 1999, Standard E10-91. Standard method of testing wood preservatives by laboratory soil-block cultures.

Further Experimental Results

Metal preservatives have a long history of use for protecting wood, but concerns have risen over the use of some metals, notably arsenic and chromium, in these systems. Organic preservatives have been proposed as alternatives, but few of these systems function well in direct soil contact. An alternative approach is to explore the use of other metal based systems. In previous tests, we have assessed the efficacy of zirconium based systems in soil block tests and found that some formulations appear to provide adequate protection. The results from analyses of blocks exposed in these tests are now described.

Materials and Methods

The wood samples were dried, ground to pass a 20 mesh screen and extracted as described below.

Wood samples were microwave digested and analyzed according to previously described procedures (Gaviak et al., 1994). Briefly, 500 mg of material was placed in a 120 ml Teflon digestion vessel. Then, 0.5 mls of trace metal grade concentrated nitric acid and 2 mls of 30% hydrogen peroxide were added. The samples were then predigested for 30 minutes, capped and micro-waved for 4 minutes at 296 watts, then 8 minutes at 565 watts power. The digested samples were transferred to a centrifuge tube and the volume was adjusted to 15 ml with deionized water prior to analyzing ICP.

Results

Weight losses from the original soil block tests are presented in Table 1. They showed that WT-292 exhibited reasonable activity against all three of the test fungi.

Metal analyses of blocks treated with WT-292 showed the metal loadings were nearly proportional to the dilutions and that metals were retained fairly well in all treatments exposed to a leaching procedure (Table 2). Both copper and aluminum were more mobile than zirconium, which appeared to be relatively leach resistant. The proportion of metal lost appeared to change with solution dilution. The proportional losses of both copper and aluminum declined with decreasing solution concentration. This decline probably reflects the availability of a limited number of binding sites. Once these sites are occupied, the remaining metal is susceptible to leaching losses and decreasing the initial solution concentration reduces this non-fixed reservoir. For example, total copper losses for the blocks treated with 5:1, 10:1 and 20:1 dilutions of WT-292 were 39, 33 and 17%, respectively, of the non-leached levels. Aluminum levels declined 25, 31 and 13%, respectively, at the same dilutions. Zirconium appeared to be very resistant to leaching losses and there was no change in loss with dilution level.

While metal migration was noted in WT-292 treated blocks, this system exhibited good activity.

TABLE 2

Copper, aluminum or zirconium contents of southern pine blocks following treatment with selected metal preservatives, leaching and 12 weeks of exposure to selected decay fungi in a soil block test:

| Chemical | Treatment Level | Leaching | Metal Levels (ppm) Cu | Metal Levels (ppm) Al | Metal Levels (ppm) Zr | Metal Levels (ppm) B |
|---|---|---|---|---|---|---|
| WT-292 | 5:1 | — | 3978 (513) | 5157 (736) | 8353 (1064) | — |
|  |  | yes | 2436 (140) | 3863 (301) | 8817 (549) | — |
|  | 10:1 | — | 2286 (113) | 2872 (212) | 5174 (350) | — |
|  |  | yes | 1539 (175) | 2002 (252) | 5243 (212) | — |
|  | 20:1 | — | 1137 (80) | 1293 (99) | 2657 (184) | — |
|  |  | yes | 954 (82) | 1132 (119) | 2627 (146) | — |

Without further elaboration the foregoing will so fully illustrate our invention that others may, by applying current or future knowledge, adapt the same for use under various conditions of service.

What is claimed is:

1. A wood preservative composition comprising an aqueous solution of inorganic polymers containing aluminum, zirconium, copper, and a fixing agent, the solution having a pH in the range of about 2.0–4.0.

2. The composition of claim 1 wherein the aluminum concentration in the final composition is approximately 3.8%–7.0% as $Al_2O_3$.

3. The composition of claim 1 wherein the zirconium concentration in the final composition is approximately 5.25%–9.1% as $ZrO_2$.

4. The composition of claim 1 wherein the copper concentration in the final composition is approximately 0.7%–8.8% as CuO.

5. The composition of claim 1 wherein the aluminum concentration in the final composition is approximately 3.8%–7.0% as $Al_2O_3$, the zirconium concentration in the final composition is approximately 5.25%–9.1% as $ZrO_2$ and the copper concentration in the final composition is approximately 0.7%–8.8% as CuO.

6. The composition of claim 1 wherein the aluminum/copper polymers have a molecular weight of approximately 1000–2000.

7. The composition of claim 1 wherein the zirconium/copper polymers have a molecular weight of approximately 6000–8000.

8. The composition of claim 1 wherein the aluminum/copper polymers have a molecular weight of approximately 1000–2000 and the zirconium/copper polymers have a molecular weight of approximately 6000–8000.

9. The composition of claim 1 wherein the fixing agent is acetic acid, sodium acetate or mixtures thereof.

10. The composition of claim 5 wherein the fixing agent is acetic acid, sodium acetate or mixtures thereof.

11. The composition of claim 8 wherein the fixing agent is acetic acid, sodium acetate or mixtures thereof.

12. The composition of claim 1 wherein the pH is adjusted using an inorganic base.

13. The composition of claim 12 wherein the inorganic base is copper carbonate.

14. A method of manufacturing the wood preservative composition of claim 1 comprising the steps of: (a) preparing an aqueous solution of a fixing agent; (b) dissolving a zirconium salt in the solution; (c) adjusting the solution pH to about 2.0 to about 4.0; (d) cooling the solution if necessary; (e) dissolving an aluminum salt in the solution; (f) dissolving a copper salt in the solution; and (g) if necessary, further adjusting the solution pH to about 2.0 to about 4.0.

15. A method of preserving wood comprising the steps of: (a) providing an aqueous suspension of the wood preservative of claim 1; (b) providing wood having at least some areas of open porosity therein; and (c) applying the suspension to the wood.

16. The method of claim 15 wherein applying the suspension to the wood is accomplished by injecting the suspension into the wood.

17. The method of claim 15 wherein applying the suspension to the wood is accomplished by immersing the wood in the suspension.

18. The method of claim 15 wherein applying the suspension to the wood is accomplished by brushing the suspension onto the wood.

19. The method of claim 15 wherein applying the suspension to the wood is accomplished by spraying the suspension onto the wood.

20. Wood impregnated with the composition of claim 1.

21. Wood impregnated with the composition of claim 1.

22. A fibrous cellulose product resistant to degradation which comprises cellulose fibers treated with an effective amount of the composition of claim 1.

23. A method of producing a cellulose fiber resistant to degradation which comprises providing an aqueous suspension of the wood preservative of claim 1 and applying the suspension to the wood.

24. The method of claim 23 wherein applying is accomplished by spraying, injecting, brushing, or immersing the suspension into the wood.

* * * * *